(12) United States Patent
Excoffier

(10) Patent No.: US 6,816,789 B2
(45) Date of Patent: Nov. 9, 2004

(54) METHOD AND SYSTEM FOR ANALYZING CHROMATOGRAMS

(75) Inventor: Jean-Louis Excoffier, Richmond, CA (US)

(73) Assignee: Varian, Inc., Palo Alto, CA (US)

( * ) Notice: Subject to any disclaimer, the term of this patent is extended or adjusted under 35 U.S.C. 154(b) by 84 days.

(21) Appl. No.: 09/839,949

(22) Filed: Apr. 19, 2001

(65) Prior Publication Data

US 2002/0182604 A1 Dec. 5, 2002

(51) Int. Cl.$^7$ .......................... G01N 33/48; C12Q 1/68
(52) U.S. Cl. ............................................ 702/19; 435/6
(58) Field of Search ................................ 702/19; 435/6

(56) References Cited

U.S. PATENT DOCUMENTS

| | | | |
|---|---|---|---|
| 5,121,443 | A | 6/1992 | Tomlinson |
| 5,905,192 | A | 5/1999 | Wikfors et al. |
| 6,195,449 | B1 | 2/2001 | Bogden et al. |

FOREIGN PATENT DOCUMENTS

| EP | 0 296 781 A2 | 12/1988 |
|---|---|---|
| EP | 0 969 283 A1 | 1/2000 |

OTHER PUBLICATIONS

Excoffier, et al., entitled "Faster Quantitative Evaluation of High–Performance Liquid Chromatography—Ultraviolet Diode–Array Data by Multicomponent Analysis", published in Journal of Chromatography, 631, (1993), pp. 15–21.

Oefner, et al., entitled "Comparative DNA Sequence by Denturing High Performance Liquid Chromatography (DHPLC)", published in American Journal of Human Genetics 57 (1995) A266.

*Primary Examiner*—Marianne P. Allen
*Assistant Examiner*—Channing S. Mahatan
(74) *Attorney, Agent, or Firm*—Bingham McCutchen LLP

(57) ABSTRACT

A method and system for chromatogram analysis is disclosed. An aspect of the invention is a method for reducing each chromatogram to a data set that can be compared to another such data set, producing a comparison result that indicates the similarity or dissimilarity of the two chromatograms. The present invention provides a system and method that can be used to identify DNA sequence variations through chromatogram analysis. The present invention also provides a user interface to display results of chromatogram analysis, which quickly and efficiently illustrates which samples are dissimilar or similar to reference chromatograms.

39 Claims, 13 Drawing Sheets

METHOD AND SYSTEM FOR ANALYZING CHROMATOGRAMS

FIELD OF THE INVENTION

The present invention relates to the field of chromatography.

BACKGROUND OF THE INVENTION

Chromatography refers to a broad range of physical methods used to separate and analyze complex mixtures. The process of a chromatographic separation takes place within a chromatography column. A solvent, either a liquid or a gas depending on the type of chromatography process employed, moves through the column and carries the mixture to be separated. As the sample mixture flows through the column, its different components will adsorb to varying degrees. The differential rates of migration as the mixture moves over adsorptive materials provide separation for components in the mixture, since different components will elute from the chromatography column at different times. A detector measures the concentration/quantity of chemical or biological components that elute from the column.

A chromatogram is a chart that shows the detected quantity or concentration of various materials eluted from the column at different times. Different peaks on the chromatogram correspond to different components in the sample mixture. The size, shape, and/or position of peaks in the chromatogram can be used to help identify the various components in the mixture.

Chromatography may be used for many types of chemical/biological analysis and separation. For example, Denaturing High Pressure Liquid Chromatography (DHPLC) is routinely used to detect sequence variations in small sections of DNA. The technique is applied to samples in which a specific DNA fragment has been amplified by Polymerase Chain Reactions. The sample is analyzed by HPLC at a temperature at which the DNA fragment is close to denaturing, at which point the chromatographic behavior changes drastically depending on the thermal stability of each fragment. If the amplified DNA fragment exhibits a sequence variation, it will denature more readily than a non-variant fragment would, and the resulting chromatogram may be noticeably different. Samples without a sequence variation, or homozygous samples with a sequence variation will have complementary DNA strands and are referred to as "homoduplex". Samples which are heterozygous for a sequence variation will form thermally less stable "heteroduplexes", in which the DNA strands are slightly mismatched.

FIG. 1 shows a portion of an example chromatographic trace 102 resulting from DNA analysis. A typical DHPLC chromatogram 102 contains a main peak 104 corresponding to leftover PCR reagents and PCR byproducts, followed by a region with one or more peaks corresponding to the DNA fragment analyzed. This region may be followed by one or more peaks resulting from the cleaning phase, in which the HPLC system gets ready for the next analysis. To detect sequence variations in the DNA mixture, analysis is performed upon the region 106 of the chromatographic trace 102 that contains the peak corresponding to the variant gene sequence. Chromatographic trace 108 is a magnified view of chromatogram 102, showing the region of interest 106 having a peak 110. Normal DNA typically corresponds to a recognizable trace pattern in region of interest 106, while variant DNA would contain a trace pattern different from the "normal" trace pattern. Thus, the particular pattern or size of the chromatographic trace in a specified region of interest can be used to separate variant DNA mixtures from normal DNA mixtures.

One approach to chromatogram classification, such as classification of chromatograms to identify the presence of sequence variations in DNA, is the "qualitative analysis" of chromatographic traces. Qualitative analysis generally refers to the analysis of chromatograms based upon the type or shape of features in the chromatographic trace. A common approach to using qualitative analysis is to perform visual examination and comparison of traces to one or more reference traces. In the example of FIG. 1, the shape of peak 110 in chromatogram 108 could be visually compared to that same region of a reference chromatogram to determine if chromatogram 108 corresponds to variant DNA. However, qualitative analysis involving visual examination is typically performed as a manual process that is often time-consuming and very subjective. Moreover, this type of approach is subject to a range of human errors.

An alternate approach is to employ "direct quantitative analysis" to classify chromatograms. The quantitative analysis approach may perform classification based upon, for example, the retention time, peak area, or number of peaks in a chromatogram trace. If an algorithm is used to count peaks in the chromatographic trace, then comparison can be made between the chromatogram of the DNA mixture being analyzed and the chromatogram of normal DNA based upon the number of peaks appearing in a region of interest in the chromatographic trace. However, a significant drawback with the direct quantitative analysis approach is that DNA sequence variations can result in changes to peak shape, rather than to the number of peaks, peak area, retention time, or other measures of direct quantitative analysis. Therefore, this approach may fail to adequately identify certain types of DNA sequence variations that affect the peak shape in chromatographic traces, particularly when DHPLC is used.

Thus, there is a need for an improved system and method to analyze chromatograms.

SUMMARY OF THE INVENTION

A method and system for chromatogram analysis is disclosed. An aspect of an embodiment of the invention provides a method for reducing each chromatogram to a data set that can be compared to another such data set, producing a comparison result that indicates the similarity or dissimilarity of the two chromatograms. In an embodiment, the present invention provides an automated system and method for identifying DNA sequence variations through chromatogram analysis. An embodiment provides a method and system for automated qualitative analysis and classification of chromatograms. One embodiment of the present invention also provides a user interface to display results of chromatogram analysis, which quickly and efficiently illustrates which samples are dissimilar or similar to reference chromatograms.

An object of the present invention is to provide a novel system and method to effectively and efficiently analyze and compare chromatograms. Another object of the invention is to provide a method and system for comparing and identifying variant DNA. Yet another object of the invention is to provide an interface for presenting chromatogram analysis results. These and other objects, advantages, and features of the invention will be apparent to those skilled in the art upon inspection of the specification, drawings, and claims.

BRIEF DESCRIPTION OF THE DRAWINGS

The accompanying drawings are included to provide a further understanding of the invention and, together with the Detailed Description, serve to explain the principles of the invention.

DETAILED DESCRIPTION OF THE INVENTION

The present invention is directed to a method and system for classifying chromatographic traces. In the specification, the invention will be described with reference to specific embodiments. It will, however, be evident that various modifications and changes may be made thereto without departing from the broader spirit and scope of the invention. For example, the invention is described with reference to analyzing chromatographic traces of DNA and with reference to identifying sequence variations in DNA samples. However, the disclosed principles of the invention are equally applicable to address other types of chromatograms and chromatographic analysis, e.g., for DNA genotyping. The specification and drawings are, accordingly, to be regarded in an illustrative rather than restrictive sense.

Figure 2:
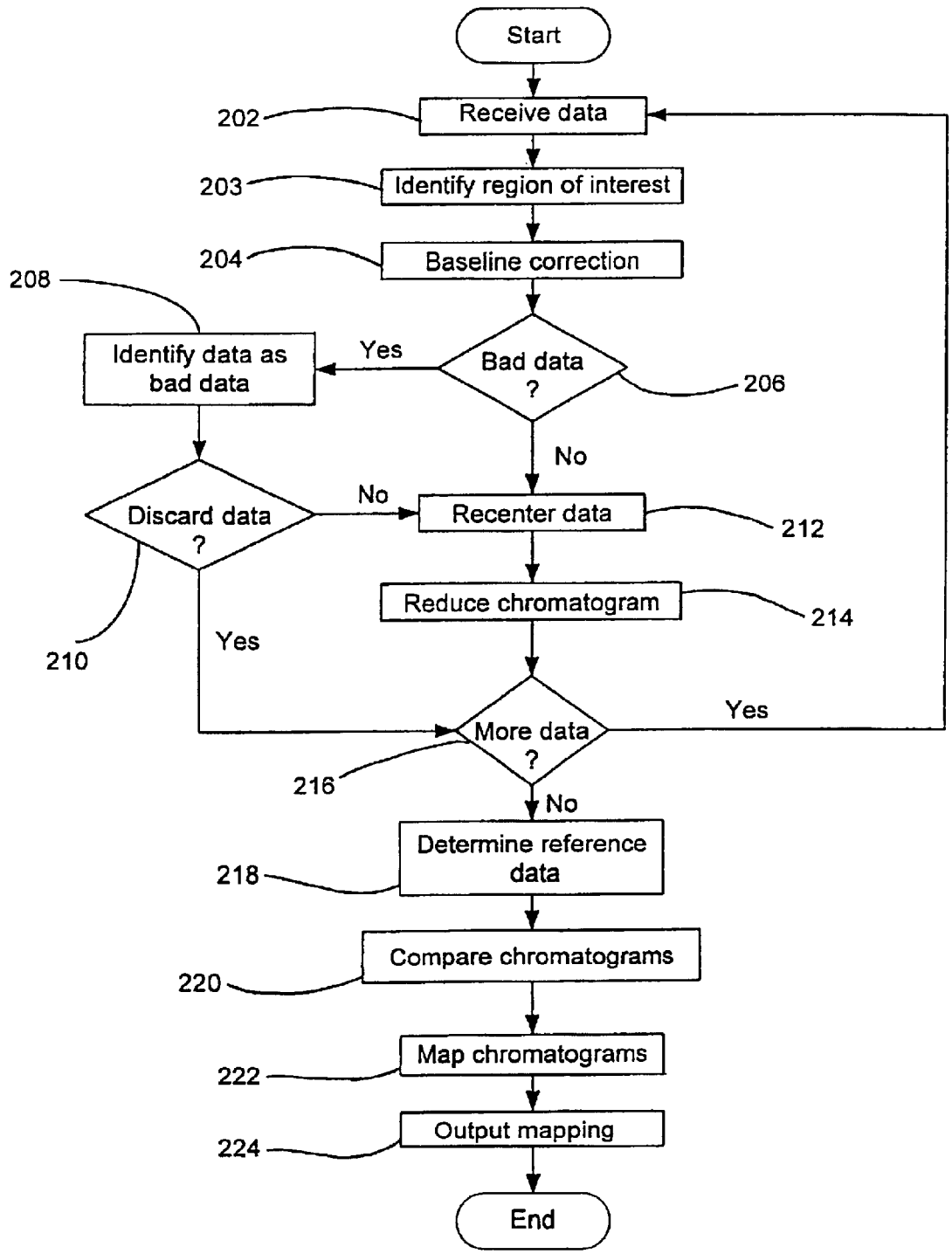
FIG. 2 shows a flowchart of a process for chromatogram analysis according to an embodiment of the invention.

One embodiment of the present invention provides a method for reducing each chromatogram to a data set that can be compared to another such data set, producing a comparison result that indicates the similarity or dissimilarity of the two chromatograms. FIG. 2 shows a flowchart of a method for analysis of DNA chromatograms according to an embodiment of the invention. At step 202, the process receives the chromatogram data to be analyzed. In an embodiment, the chromatogram data comprises a chromatogram data file, in which the data file corresponds to digitized data for a chromatographic trace of a specific DNA sample mixture.

Figure 1:
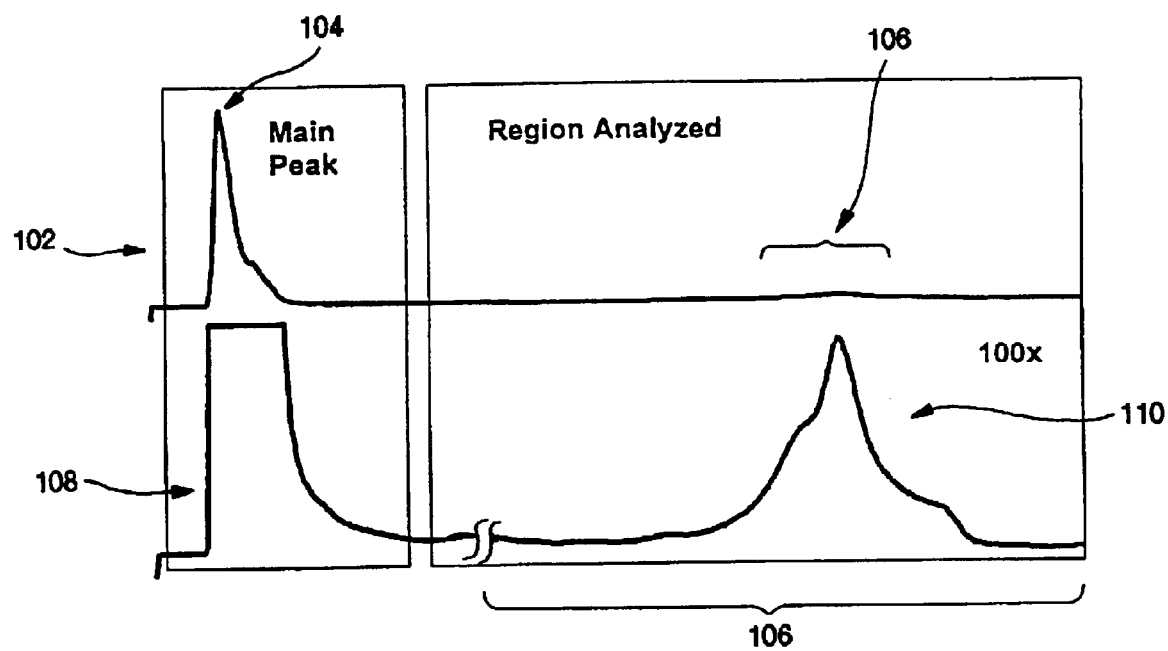
FIG. 1 depicts an example chromatographic trace.

A region of interest in the chromatographic trace is identified for the chromatogram data (203). According to an embodiment of the invention directed to DNA analysis, the selected region of interest should exclude the main DNA peak corresponding to PCR Reagents and byproducts, while fully encapsulating the portion of the chromatographic trace that potentially contains a peak corresponding to a variant gene sequence (e.g., the region of interest 106 in FIG. 1). The specific region of interest employed in the invention depends upon numerous factors, such as the type of biological/chemical material analyzed, the type of chromatography system employed, the type of analysis being performed, and the conditions under which chromatographic separation takes place. For example, a time range of 2 to 4 minutes may be employed for certain types of DNA analysis using a dHPLC chromatography system. In many DNA chromatograms, the amplitude of the signal in the region of interest may be approximately two orders of magnitude lower than the amplitude of the main peak, corresponding to PCR Reagents and byproducts.

In an alternate embodiment, a specific region of interest in the chromatogram does not have to be identified. Instead, in an embodiment, the data collection process is configured such that the collected or received chromatogram trace data only includes regions of interest to the analysis process. This may be accomplished, for example, by only recording chromatogram trace data during specified periods of the chromatography process when it is known that relevant data will be produced. Alternatively, the entire chromatographic trace is employed in the present classification process without identifying any particular regions of interest.

Figure 3A:
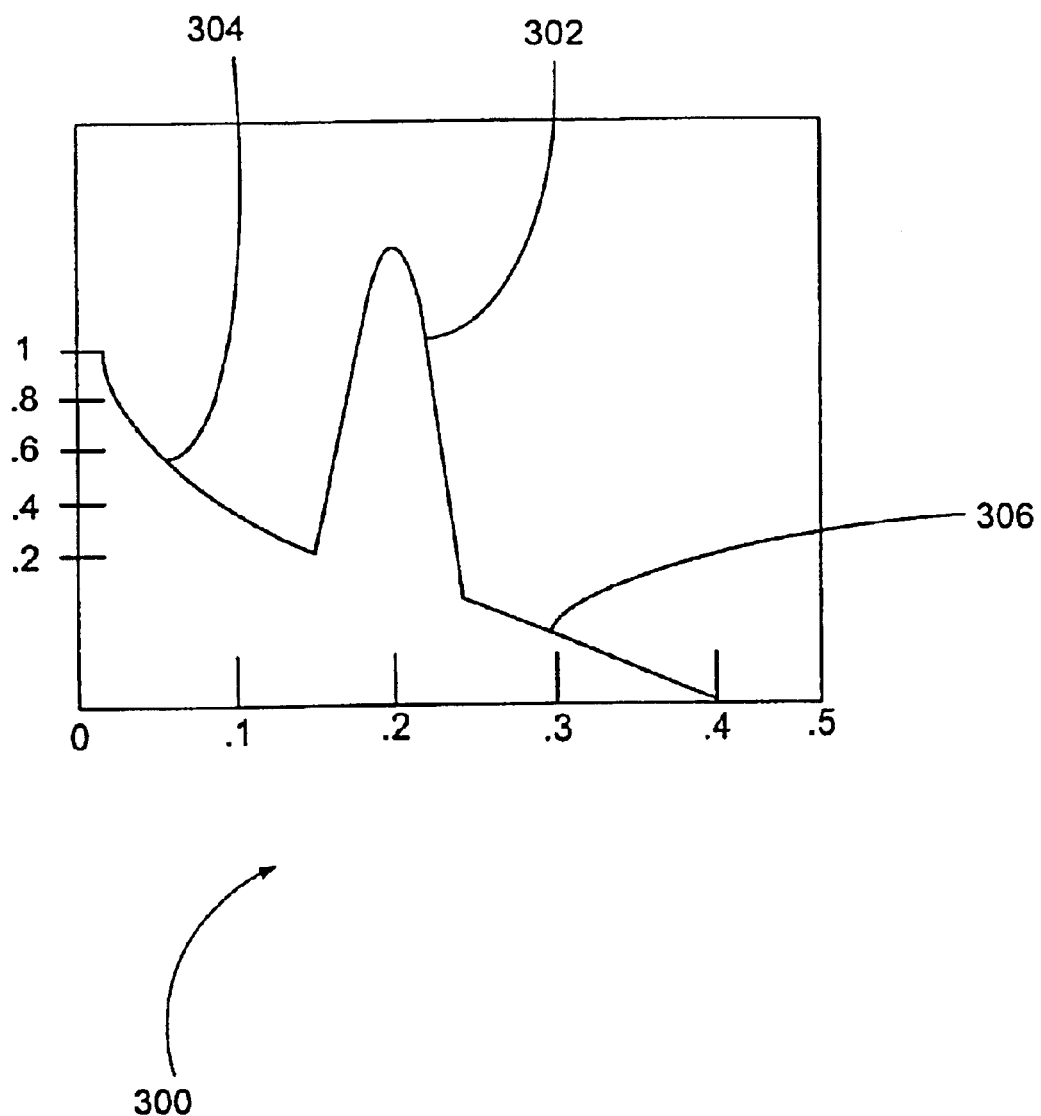
FIGS. 3a, 3b, 3c, and 3d illustrate a method for baseline correction according to an embodiment of the invention.

Baseline correction is performed to normalize the chromatogram data for the identified region of interest (204). To further describe baseline correction, reference is made to FIG. 3a, which illustrates the region of interest 300 for an example DNA chromatogram. Region of interest 300 includes a peak 302. The preceding portion 304 of the chromatographic trace extends from the main DNA peak to peak 302, and a trailing portion 306 of the chromatographic trace extends from the trailing edge of peak 302. Note that both the preceding portion 304 and the trailing portion 306 of the chromatographic trace in the region of interest 300 comprises a slope, shape, and area. Baseline correction is the process of isolating peak 302 from characteristics of the rest of the chromatographic trace, such as the slope, shape, or area associated with the preceding portion 304 and trailing portion 306 in the region of interest 300.

Figure 3B:
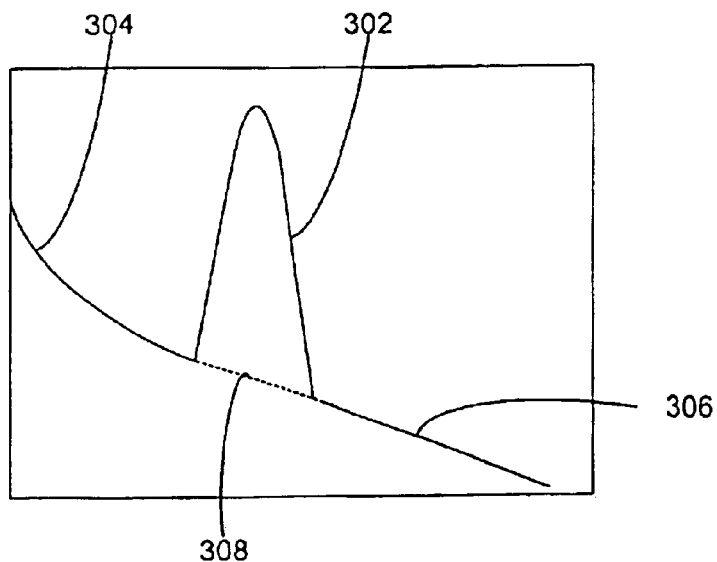
Figure 3C:
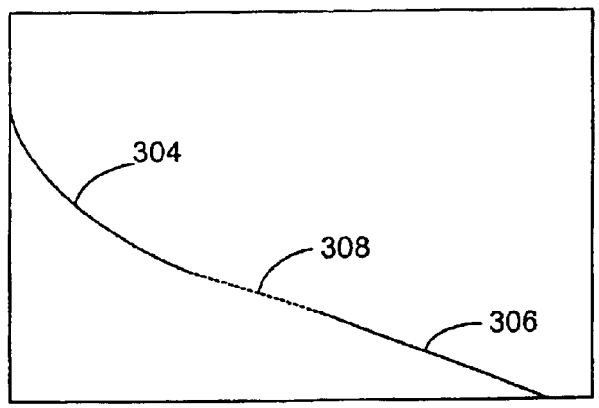
Figure 3D:
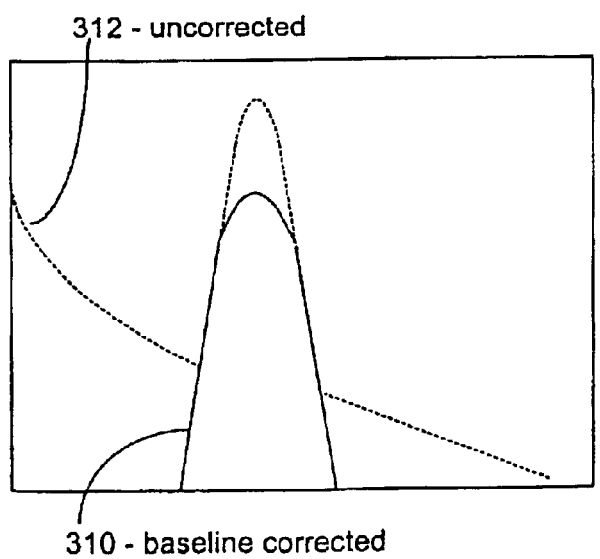

FIGS. 3b, 3c, and 3d graphically illustrate a process for baseline correction according to an embodiment of the invention. Referring to FIG. 3b, the first action of the baseline correction process is to extend the lowest point of the preceding portion 304 of the chromatographic trace to the highest point of the trailing portion 306. This new extension 308 cuts through the lower portion of peak 302. FIG. 3c depicts the shape of the chromatographic trace if only portions 304, 306, and extension 308 are considered. To perform baseline correction, the shape shown in FIG. 3c is subtracted from the shape shown in FIG. 3a to generate the baseline-corrected shape 310 as shown in FIG. 3d. The original shape 312 of the uncorrected trace 302 is shown as a dotted line in FIG. 3d.

The process illustrated in FIGS. 3b, 3c, and 3d can be implemented by starting with the first point in the data array corresponding to the chromatographic trace, and considering the straight lines joining this point to each of the subsequent points in the array. The baseline correction process uses the lowest line of the set to baseline-correct the data between the previous point and the point that produces the lowest line. These steps are repeated starting with this point, until the end of the array is reached. The baseline could be determined on a filtered array, e.g., a 3 or 5 point moving average. Alternatively, peak limits can be identified in the chromatographic trace and used to determine a baseline. In an alternate embodiment, baseline correction is not performed in the present classification process.

When chromatogram data is collected for a DNA sample, it is possible that errors may occur during the chromatography process. These errors may cause the recorded chromatographic trace for that particular sample to be "bad" or flawed data. Through experimentation, it is possible to identify a range of characteristics for a peak in the region of interest that corresponds to valid, non-erroneous data. Referring back to FIG. 2, a "bad data filter" could be employed to determine if a particular chromatographic trace corresponds to flawed data (206). Some of the characteristics that could be checked by a bad data filter include the height, shape, size, position, and/or slope of a peak in the region of interest. One or more threshold values could be established for the characteristics of the peak checked by the bad data filter. If the chromatographic trace contains a peak that exceeds a threshold characteristic, then the data is identified as "bad" data (208). Bad data can either be eliminated from the set or retained (210). If bad data is eliminated, then additional chromatogram data is received and the process described above is repeated for the additional data (216). If the bad data retained, then the identification of a particular set of data as being "bad" is maintained and used with respect to the selection of a reference data set, as described in more detail below.

Within the identified region of interest, it is possible that the peak may appear in different locations for different chromatograms. This may be caused, for example, by minor variations in the conditions under which chromatographic separation takes place. To facilitate comparisons between different chromatograms, the positional data for peaks in different chromatograms can be analyzed consistent with each other. One approach for consistent peak analysis is to perform the analysis relative to a recognized reference position or offset for the different chromatogram peaks. In the preferred approach, the classification process re-centers the chromatogram data in the region of interest (212). Re-centering the chromatogram data mathematically causes the "window" of data corresponding to the region of interest to be centered around the peak location for each chromatogram. This re-centering inherently causes the peaks position within the regions of interest to be consistent from one chromatogram to the next.

Figure 4:
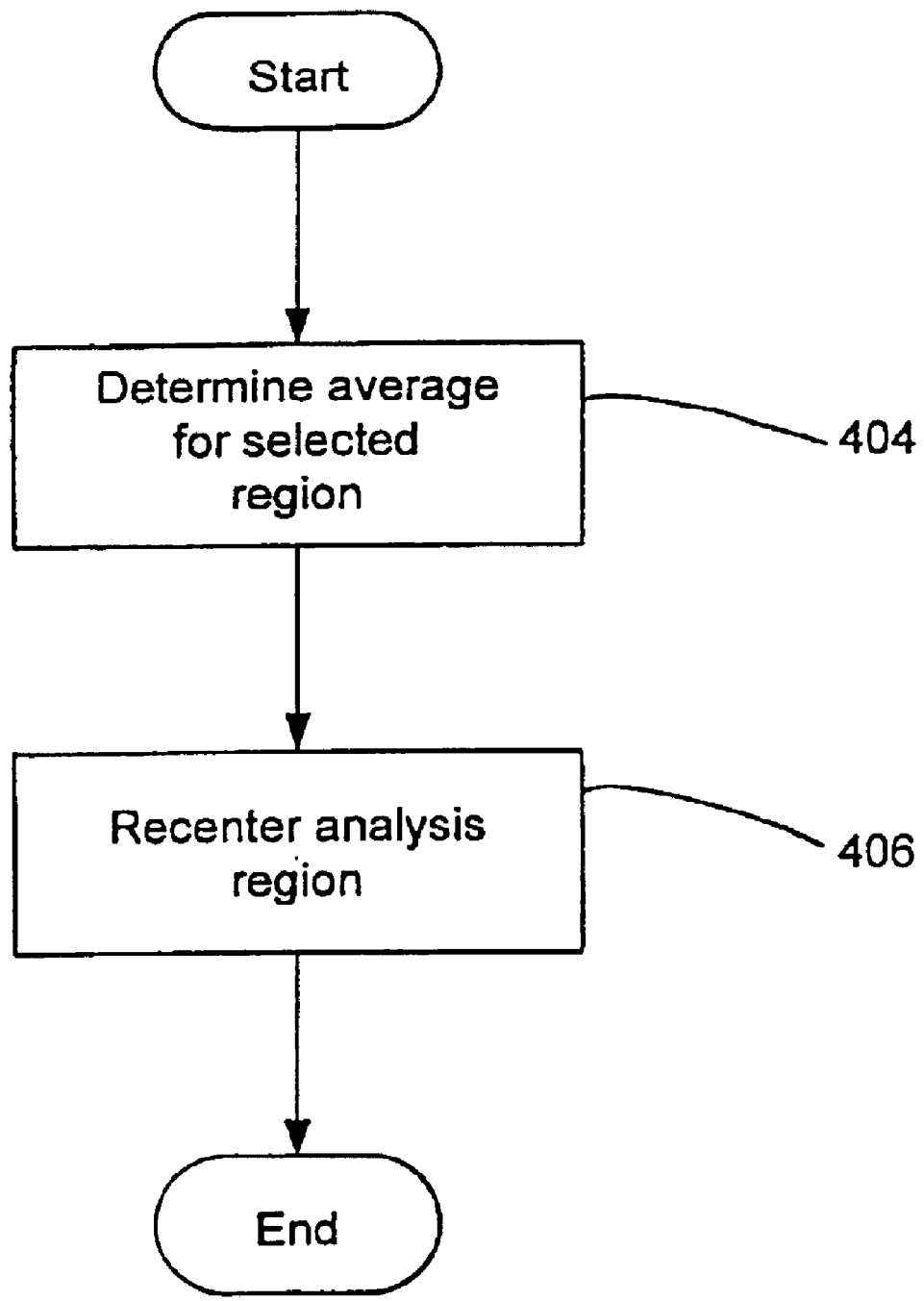
FIG. 4 shows a flowchart if a process for re-centering an analysis window according to an embodiment of the invention.

FIG. 4 shows a flowchart of a process for re-centering chromatogram data according to an embodiment of the invention. At 404, the average time for the region of interest is determined. One approach for determining the average time is as follows:

$$\bar{t} = \left(\sum_{i=0}^{i=n} yi^2 * t_i\right) / \sum_{i=0}^{i=n} yi^2 \quad \text{(Eq. 1)}$$

where $y_i$ and $t_i$ are the amplitude and time, respectively, for point i. The square of the amplitude is adopted in this approach to minimize the influence of noise and baseline fluctuations. The average time value is utilized to re-center the analysis region for the chromatography trace (406). The analysis window for the chromatogram is shifted along the time axis such that average time forms the center position of the shifted analysis window.

Figure 5A:
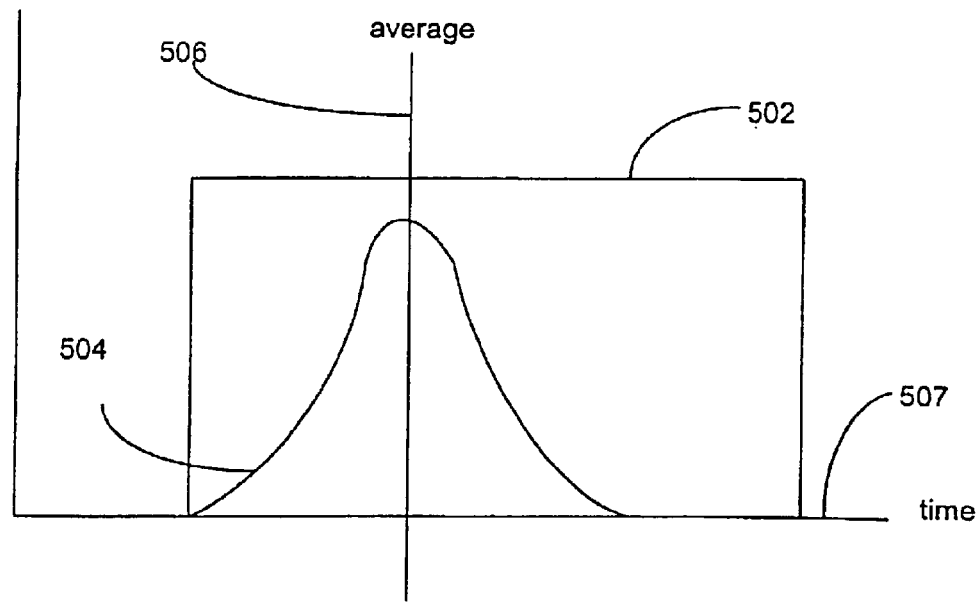
FIGS. 5a, 5b illustrate a method of re-centering an analysis window according to an embodiment of the invention.
Figure 5B:
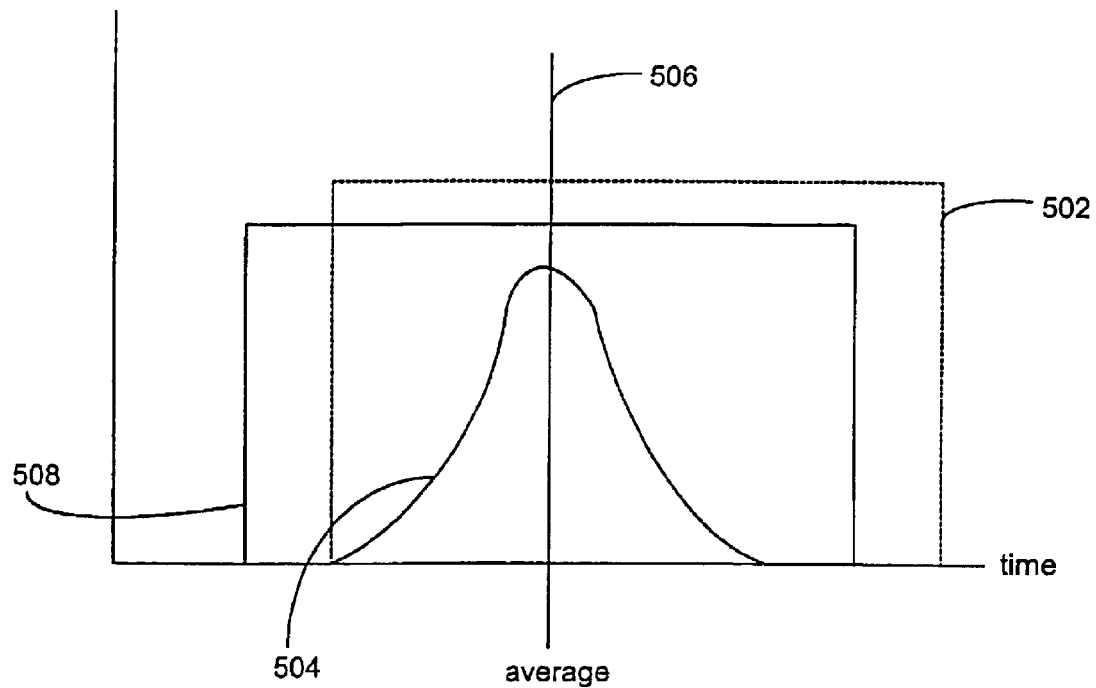

FIGS. 5a and 5b graphically illustrate a process for re-centering according to an embodiment of the invention. Referring to FIG. 5a, shown is an analysis window 502 surrounding a region of interest for an example chromatography trace 504. The average time location for the amplitude values of trace 504 is noted by positional line 506 along the time axis 507. It can be seen that the average positional line 506 in trace 504 is not centered within window 502. To re-center the analysis window, window 502 is shifted along the time axis 507 such that the time position of the average positional line 506 forms the center of window 502. FIG. 5b shows the results of the re-centering process, in which analysis window 508 surrounding the region of interest in trace 504 is centered around the average position 506, i.e., the portion of analysis window 508 located to the left of the average position 106 approximately equals the portion of window 508 located to the right of average position 506. The former location of window 502, prior to the re-centering process, is shown in dotted lines.

Referring back to FIG. 2, the next step is to reduce the chromatographic trace to a standardized data set that can be compared numerically to other data sets (214). In an embodiment, this is performed by generating a data set for each chromatogram comprised of an array of values representative of, or derived from, the baseline-corrected and centered trace in the region of interest.

In a first approach, this data set is directly formed using the chromatogram data for a trace in the region of interest; that is, the data set comprises an array of (time$_n$,amplitude$_n$) values, where time$_n$ represents the time at a particular point n along the time axis and amplitude$_n$ represents the amplitude of the trace at that time$_n$. A common set of n time points are used to determine this array of values for each chromatographic trace. Each data set can be compared or correlated to data sets for other chromatographic traces.

An alternate approach uses a "distribution" method to generate a data set for each chromatographic trace. In this approach, the integral of a chromatogram signal within the selected time region is calculated and plotted against a time axis. The integral of the chromatogram signal equates to the area formed by the chromatogram at a given point in time. To reduce the influence of noise, the integral of the square of the chromatogram signal in the region of interest can be calculated and plotted against the time axis, as follows:

$$Area(n) = \sum_{j=0}^{j=n} y_j^2 \quad \text{(Eq. 2)}$$

where y represents the chromatogram signal at a given point j, and area(n) is the area formed by the chromatographic trace from the starting point up to the jth point within the time region. The total area will be the area formed by the chromatographic trace within the entire time region.

Figure 6A:
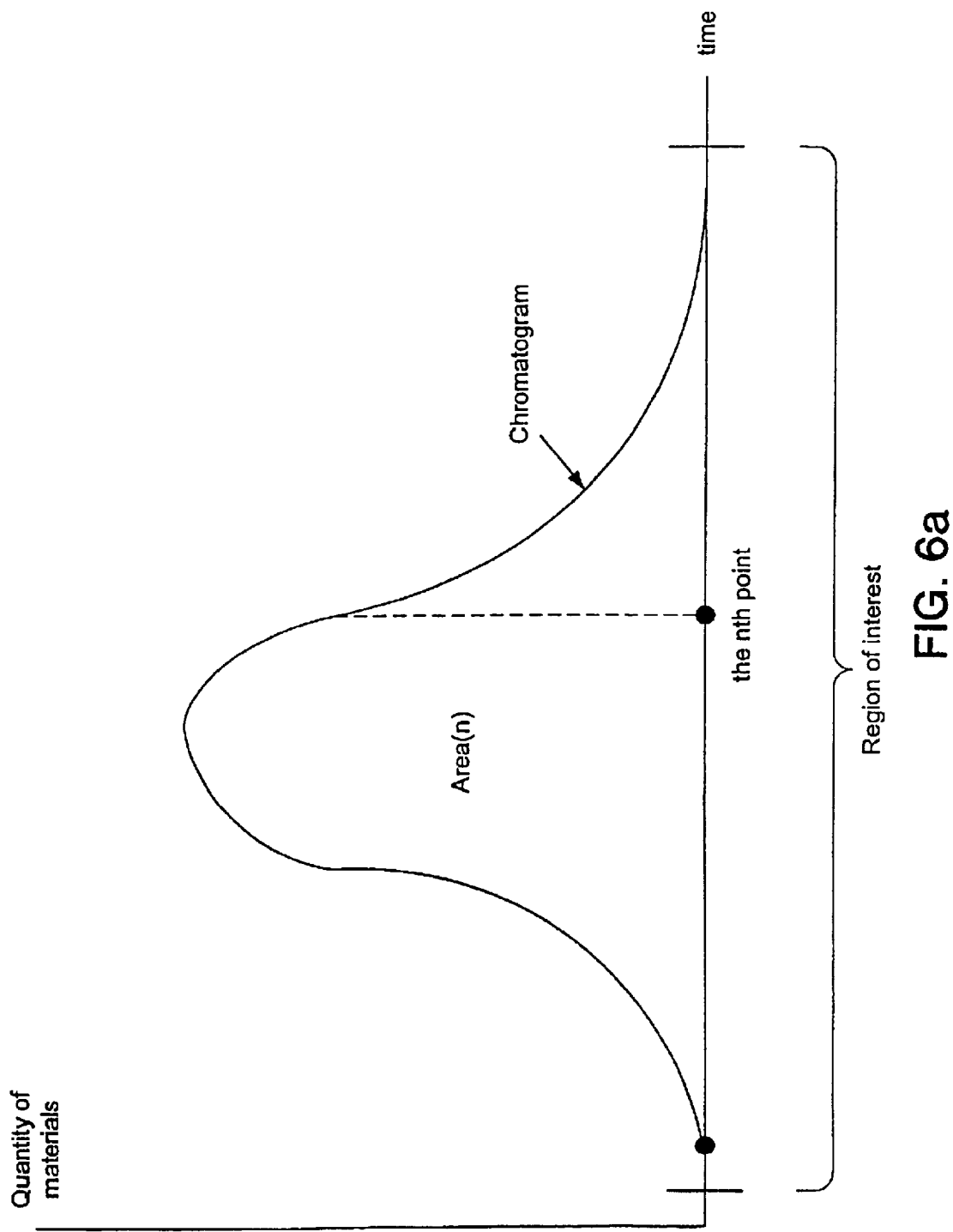
FIG. 6a illustrates calculations for the area under a chromatographic trace.
Figure 6B:
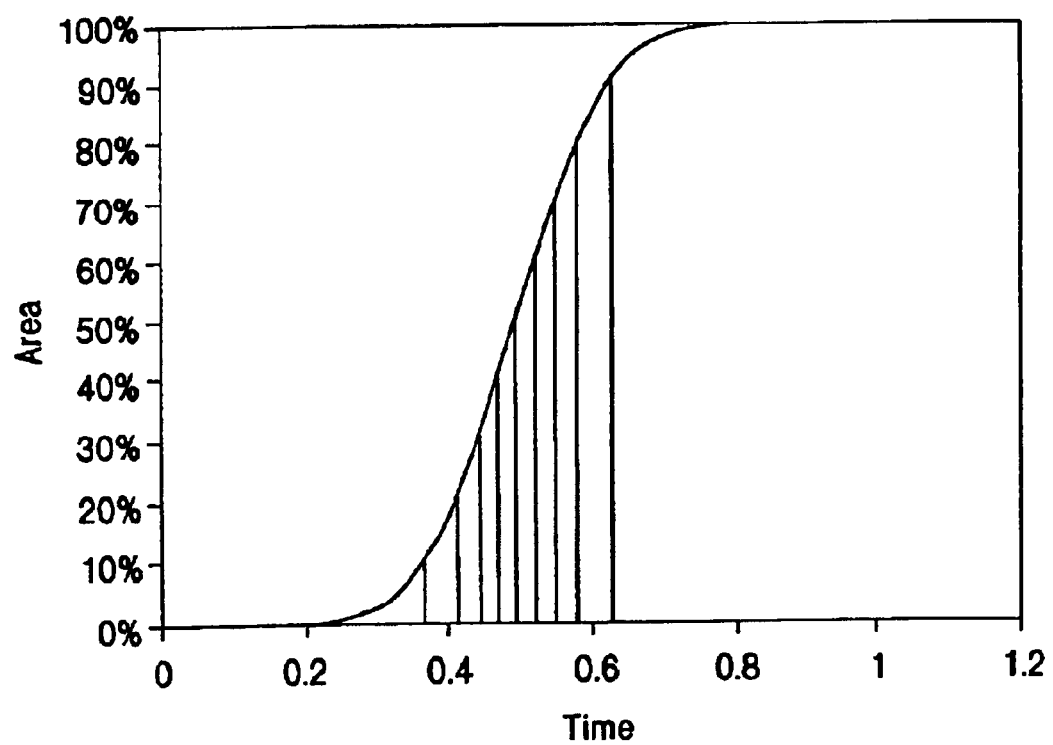
FIG. 6b illustrates chromatogram reduction according to an embodiment of the invention.

This area determination of a trace for a region of interest is illustrated in FIG. 6a. The area(n) can be plotted against a time axis as shown in FIG. 6b. A set of time values is identified to divide the area into N equal slices. FIG. 6b illustrates a set of 10 slices for the plotted (time,area) values, based upon the percentage of the area for the trace at a given point in time. The time values can be refined by linear interpolation between the data points that bracket the target values. For instance, if the area up to point j at 0.36 minute is 8.84% of the total area and the area at point j+1 at 0.37 minute is 10.56% of the total area, the time value for the 10% mark is then 0.36+0.01*(10−8.84)/(10.56−8.84)= 0.3667. In an embodiment, the 0% and 100% values, which are the start and end of the integrated array, are discarded. The values are normalized so that the first data point is 0 and the last one is 1 using a linear transformation. The resulting data set represents the distribution of area in the selected region.

Under certain circumstances, the direct comparison approach may be more sensitive to the proper alignment of the data, and therefore small imperfections in the time alignment process could have a significant impact in the correlation process. Thus, the distribution method may work better with data that have sharp features such as narrow peaks, while the direct comparison may work better with data that has broad features. One approach to reduce the sensitivity of the direct comparison method to time alignment is by shifting one data set relative to the other to vary their overlap and determine the optimal correlation value. This can be done instead of or in addition to the Reference Time approach.

Other approaches may also be employed to reduce each chromatographic trace in the region of interest to a suitable data set. For example, the slope or curvature of the chromatogram signal, with or without averaging or smoothing, may be employed and combined to generate a data set representative of the chromatographic trace in a region of interest.

Referring back to FIG. 2, the process thereafter determines whether more chromatogram data needs to be processed (216). If so, then the previous process actions shown in FIG. 2 are repeated for each additional item of chromatogram data. If not, then the process selects a reference chromatogram from all of the previously processed chromatographic traces (218). The data set corresponding to the selected reference chromatogram provides a baseline that is compared against data sets for all other traces being analyzed. For DNA analysis, the result of the comparisons provides an indication of whether sequence variations exist in DNA samples. Thus, in an embodiment, the reference chromatogram is selected to be the trace that corresponds most closely to characteristics indicative of "normal" DNA.

Figure 7A:
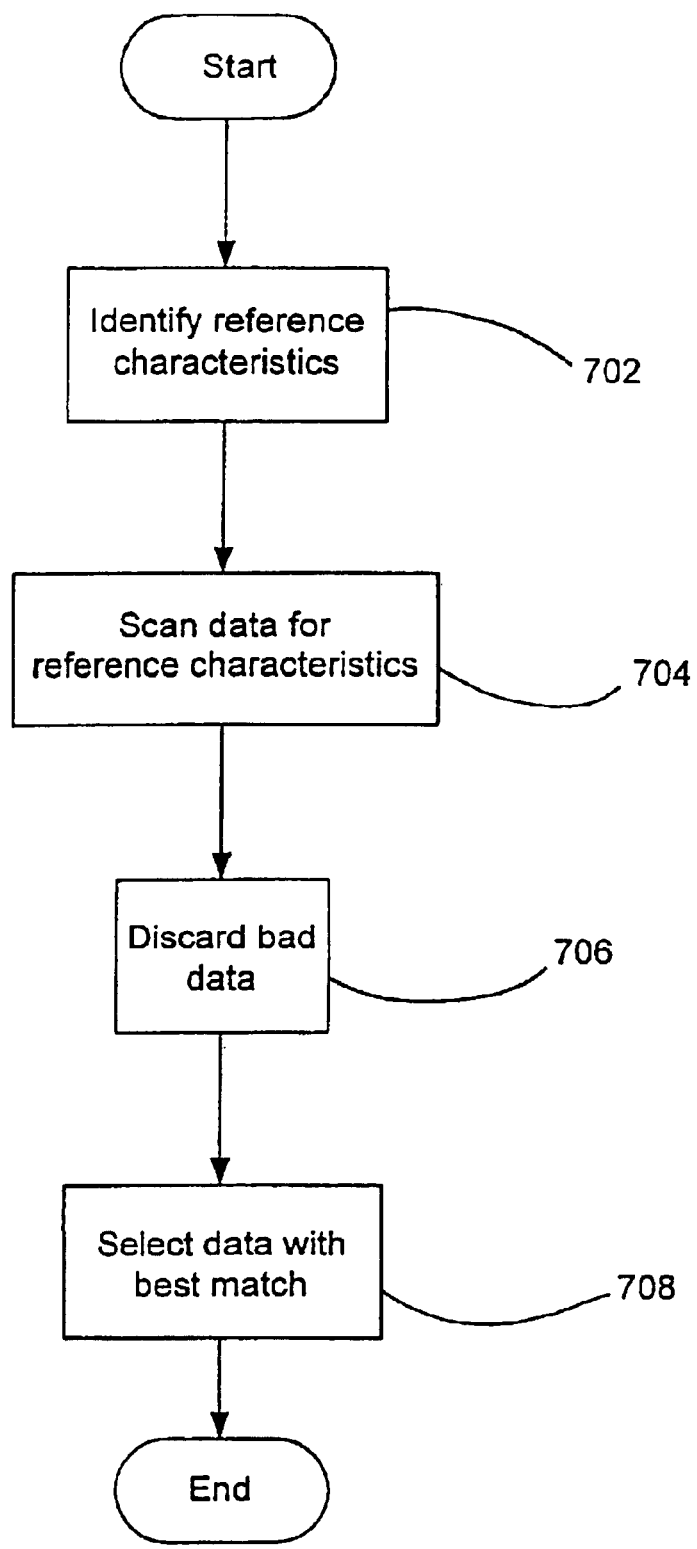
FIGS. 7a and 7b show flowcharts of method for selecting a reference data set according to embodiments of the invention.

FIG. 7a shows a flowchart of a process for selecting a reference chromatogram according to an embodiment of the invention. At 702, the ideal characteristic(s) of a normal trace pattern in the region of interest is identified. For example, for DNA analysis, the ideal characteristic for a normal trace pattern may comprise the chromatogram having the lowest variance in time. This variance could be represented as the width of the chromatographic features, and the reference chromatogram (or "homoduplex" reference) is the chromatogram having the simplest and narrowest trace.

The entire set of baseline-corrected and centered chromatogram data is examined for the one trace that most closely matches the ideal characteristics (704), e.g., having the lowest variance in time. Variance may be calculated according to the following, in an embodiment:

$$\bar{t} = \sum_{i=0}^{i=n} yi^2 * t_i \bigg/ \sum_{i=0}^{i=n} yi^2 \quad \text{(Eq. 3)}$$

$$v = \sum_{i=0}^{i=n} yi^2 * (t_i - \bar{t})^2 \bigg/ \sum_{i=0}^{i=n} yi^2 \quad \text{(Eq. 4)}$$

where v represents the variance, and $y_i$ and $t_i$ are the amplitude and the time, respectively, for to point i. Other approaches may be used in the invention to calculate variance. For example, equations 3 and 4 could be modified such that variance is computed based upon either the amplitude $y_i$ or the square of amplitude $y_i^2$, for each point i.

In an embodiment, chromatogram data previously identified as being "bad data" is excluded from being eligible for selection as the reference chromatogram (706). The chromatogram having the closest match to the identified characteristics is selected as the reference chromatogram (708). Thus, for an embodiment of the invention for DNA analysis, the chromatographic trace having the lowest variance in time, which was not previously identified as being bad data, is selected as the homoduplex reference chromatogram.

Under certain circumstances, the chromatographic trace that most closely matches the "ideal" characteristics of a normal chromatogram may not actually be the most "normal" data set, e.g., because of abnormalities in the data set indicating best match which disguises other abnormal characteristics. For example, if the low-variance characteristic is the only criteria used to select the reference DNA chromatogram, then it is possible that a trace with an abnormally narrow peak is chosen as the homoduplex reference.

Figure 7B:
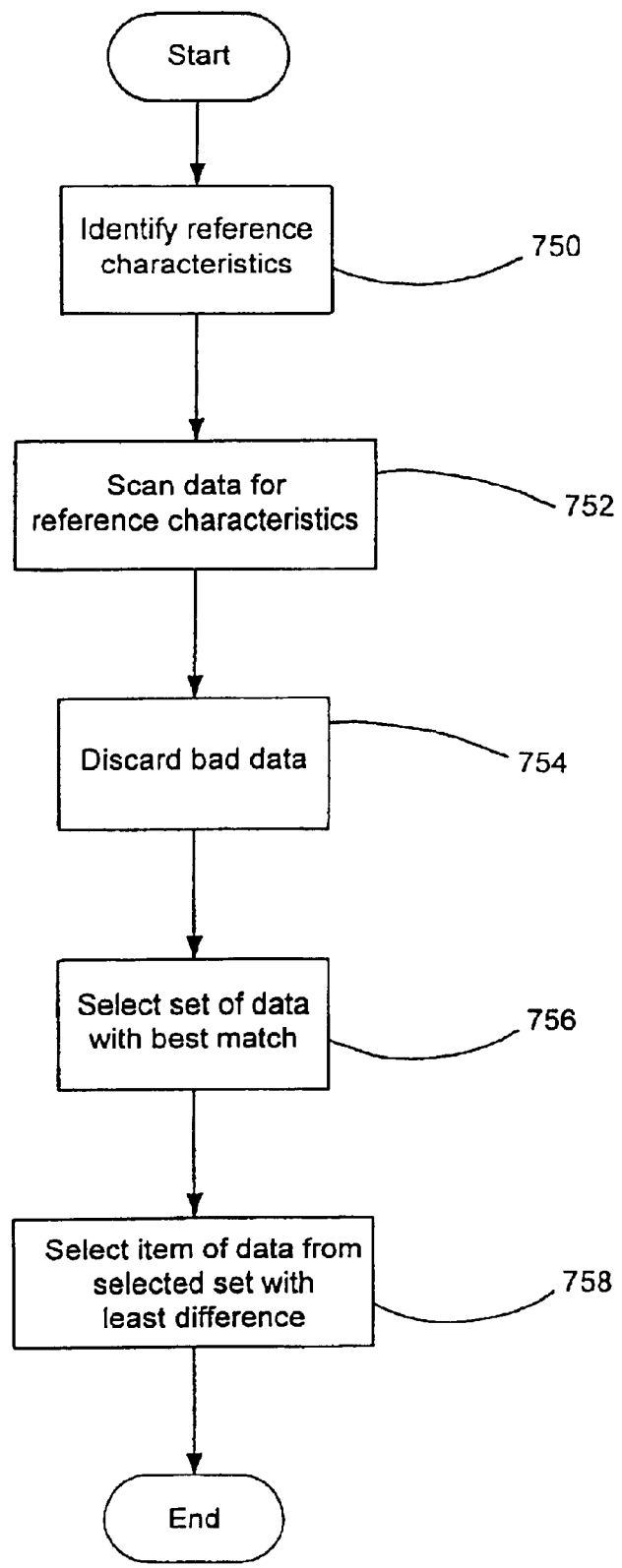

FIG. 7b shows a flowchart of an alternate approach to select a reference chromatogram. In this approach, the ideal characteristic(s) of the reference chromatogram are again identified (750), like the approach of FIG. 7a. The set of chromatogram data is scanned to identify chromatographic traces that correspond to the ideal characteristic(s) (752). As before, identified bad data is excluded from eligibility from being selected as the reference chromatogram (754). However, instead of selecting only a single chromatogram that corresponds to the ideal characteristics, multiple chromatograms that most closely match the ideal characteristics are identified (756). For example, five chromatograms may be selected that most closely match the ideal characteristics. If low variance is the desired characteristic, then this step identifies N samples with the lowest variances in time. Each of the selected traces are compared with the other traces in the set, and the trace having the least dissimilarity with the other traces is selected as the reference trace (758). This comparison can be performed, for example, by plotting the vector for each trace data set and calculating the offset difference between each trace vector; the trace with the least dissimilarity is identified based upon the smallest total distance to the other plotted traces.

With reference back to FIG. 2, the next step in the process is to compare each of the chromatograms against the reference chromatogram (220). Any approach to comparing or correlating two sets of values may be employed to compare the chromatograms. In an embodiment, the comparison of data sets can be conducted by using a correlation coefficient which measures the cosine of the angle (i.e., similarity) between the two data sets, as follows:

$$\text{Cos}(A, B) = \frac{\sum_{i=0}^{i=n} A_i * B_i}{\sqrt{\sum_{i=0}^{i=n} A_i^2 * \sum_{i=0}^{i=n} B_i^2}} \quad \text{"Similarity" Equation (Eq. 5)}$$

where A represent a first chromatogram data sat and B represents a second chromatogram data set.

An alternate approach is to determine the sine value of the angle (i.e., the dissimilarity), as follows.

$$\text{Sin}(A,B) = \sqrt{1 - \text{Cos}^2(A,B)} \quad \text{"Dissimilarity" Equation (Eq. 6)}$$

A third approach is to determine the distance between the vectors. After normalization, the data set of each chromatographic trace is unit length vector that terminates on the hypersphere of a unit diameter. If θ is the angle between the two vectors A and B, then the Euclidian distance between the tips of these vectors can be expressed as D=2*sin θ/2. The distance can therefore be as a function of the cosine of the angle:

$$D(A, B) = 2^* \sqrt{\frac{1 - \cos(A, B)}{2}} \quad \text{"Distance" Equation (Eq. 7)}$$

which can also be expressed as:

$$D(A,B) = \text{SQRT}(2(1-\cos(A,B))) \quad \text{(Eq. 8)}$$

The distance equation takes values of 0 for identical data sets and Sqrt(2) for orthogonal data sets. To make the calculations more user-friendly, the "2" can be removed from the equation to obtain a simplified distance value varying from 0 to 1, with otherwise equivalent properties:

$$d(A,B) = \text{SQRT}(1-\cos(A,B)) \quad \text{(Eq. 9)}$$

A distance-based correlation value can be defined as:

$$DBC(A,B) = 1 - d(A,B) \quad \text{(Eq. 10)}$$

This equation has the usual properties of a correlation, in which it varies from "1" for identical sets to "0" for orthogonal sets.

Once all of the chromatogram samples have been compared against the reference chromatogram, the sample that is the most different can be selected as the "heteroduplex" reference. Alternatively, the heteroduplex reference can be manually selected.

Figure 8:
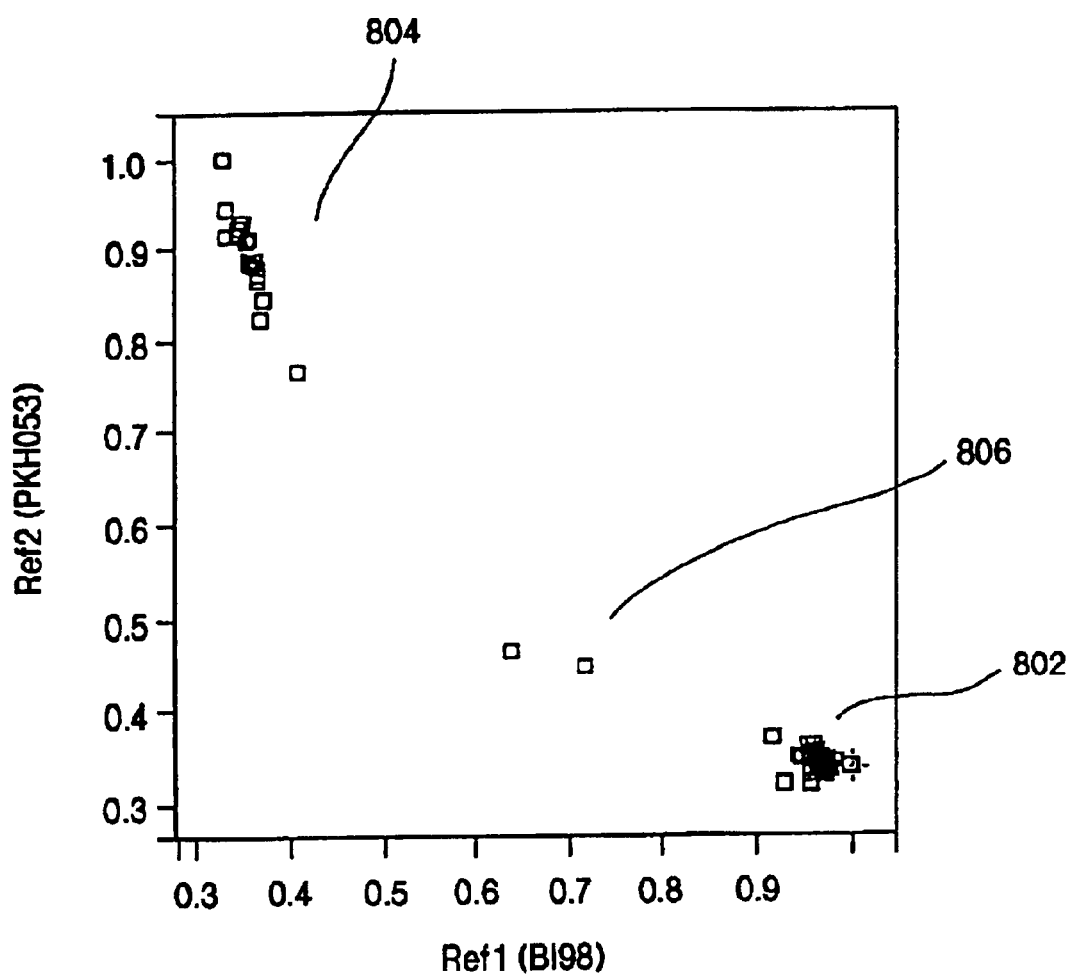
FIG. 8 illustrates an approach to chromatogram mapping according to an embodiment of the invention.

The comparisons between each chromatogram sample and the reference chromatograms can be plotted and mapped (222 and 224). FIG. 8 depicts a two-dimensional cluster map 800 in which each sample is represented by the values of its similarity (measured by DBC) with Reference 1 (Homoduplex) and Reference 2 (Heteroduplex). The example cluster map 800 in FIG. 8 illustrates a tight cluster of homoduplex samples 802, a well-separated cluster of heteroduplex samples 804, and some isolated points 806 that do not directly correspond with either the homoduplex or heteroduplex references.

The results of the mapping operation provide an immediate visual indication of samples that are likely to contain or not contain sequence variations. Automated procedures can be established to sort and identify samples that either contains or does not contain sequence variations, based upon either the numeric results of the comparisons or based upon the results of the mapping operation, e.g., by establishing threshold distance values from the homoduplex or heteroduplex reference points. This highlights a particular advantage of the present invention, in which automated procedures can be performed to analyze and identify chromatograms according to a set of defined criterion, rather than requiring a manual process of subjective visual examinations.

If different types of sequence variations are present, it is possible to identify multiple clusters on the map based on distance and standard deviation. Clusters around the homoduplex and heteroduplex references are homogeneous clusters, because samples in each cluster are similar to the same reference. However, a cluster in the middle of the map may not be homogeneous. The fact that two samples have roughly the same correlation values with the two references does not indisputably establish that these samples are similar. Therefore, a cluster found in the middle of the map may need to "validated", which could be done by verifying that all the 2 by 2 comparisons within the cluster lead to a sufficient threshold of similarity. Thus, if comparisons between any two samples within the cluster demonstrate a sufficient similarity, the cluster being analyzed can be considered valid. Otherwise, the samples in the cluster can be reprocessed by selecting new reference and repeating the above actions of comparing chromatograms and mapping the results.

Figure 9:
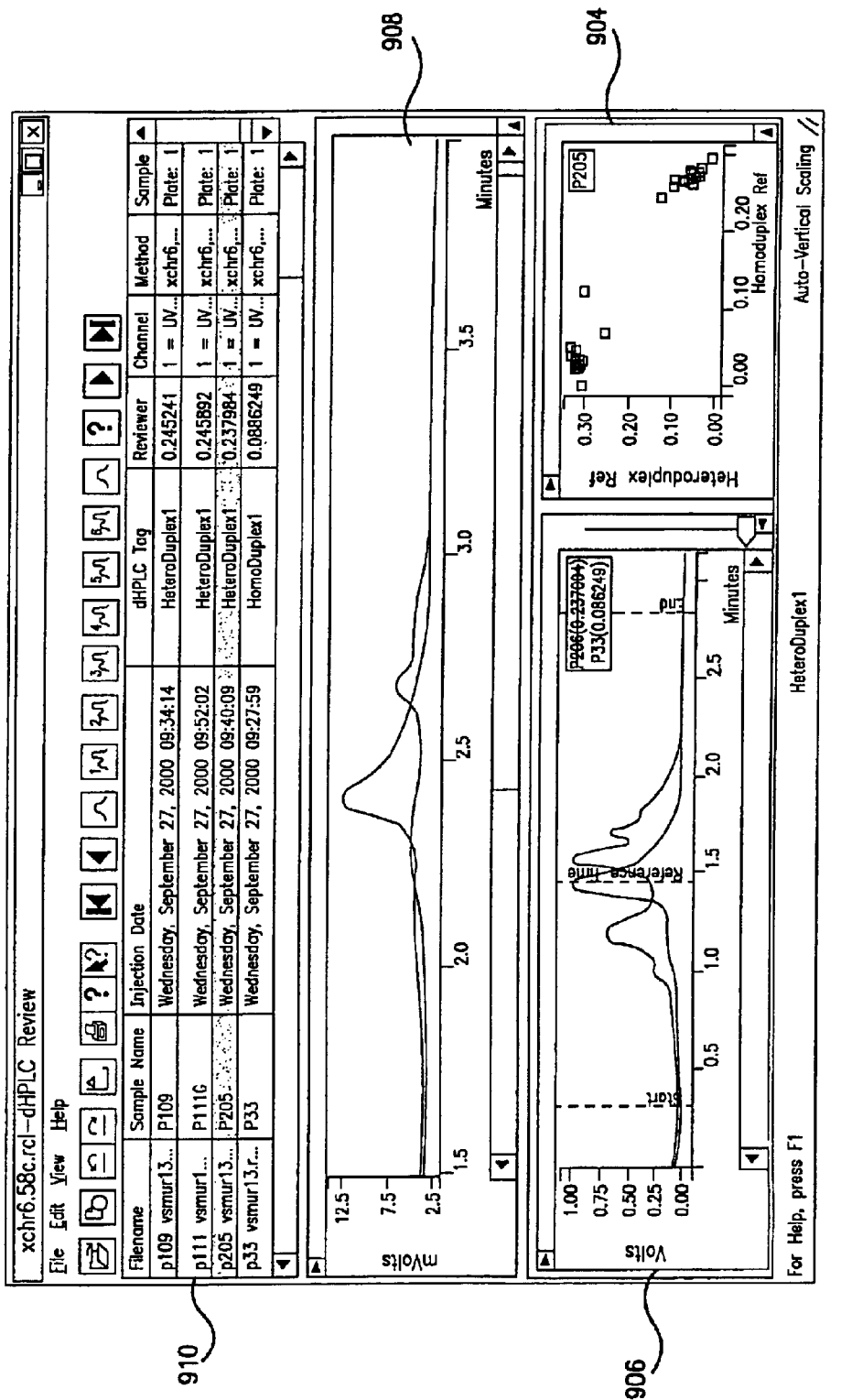
FIG. 9 depicts a user interface according to an embodiment of the invention.

FIG. 9 depicts a user interface 902 for analyzing chromatograms according to an embodiment of the invention. User interface 902 comprises a cluster map portion 904 for displaying the results of comparing/correlating chromatographic traces, such as the cluster map shown in FIG. 8. The baseline-corrected and centered traces are displayed in a window 906. Raw chromatographic trace data (e.g., without re-centering) can be displayed in another window 908. A list of the chromatogram data files can be displayed in another window 910.

In an embodiment, user interface 902 is configurable to permit users to zoom in and out of each window. For example, each portion of cluster map 904 can be magnified to display individual mapped points. Features in cluster map 904 can be minimized to permit display of the entire cluster map. In an embodiment, selecting one or more points on cluster map 904 will display the corresponding chromatographic trace(s) in windows 906 and/or 908. As illustrated in FIG. 9, multiple chromatographic traces may be overlaid above each other to allow visual comparison of the traces. The traces can be automatically selected and overlaid based upon identified selection criteria. For example, threshold values may be established to determine which points on the cluster map 904 correspond to a homoduplex cluster or a heteroduplex cluster. The system may be configured to automatically display the traces for each cluster based upon user selection of the desired cluster. Other and additional criteria may be established for automated overlaying of one or more traces within the scope of the invention.

Figure 10:
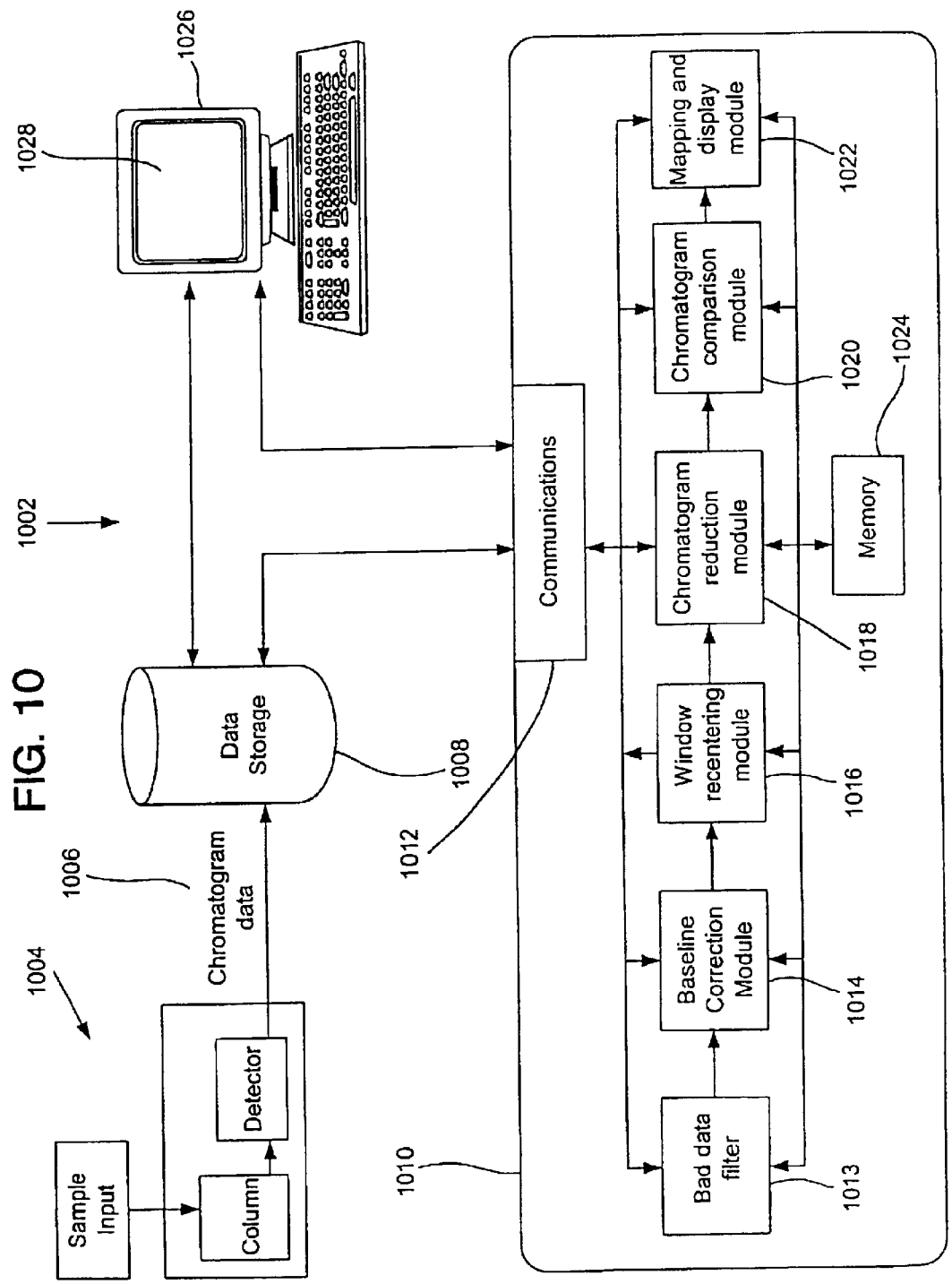
FIG. 10 shows a system for chromatogram analysis according to an embodiment of the invention.

FIG. 10 depicts a system 1002 for chromatogram analysis according to an embodiment of the invention. System 1002 comprises a chromatography system 1004 that generates chromatogram data 1006, which is stored in a data storage device 1008. System 1002 further comprises a chromatogram analysis module 1010 pre-configured or configurable to perform some or all of the process actions of FIG. 2. Chromatogram analysis module 1010 includes a communication interface 1012 for sending and receiving data from data storage device 1008. Chromatogram analysis module includes a baseline correction module 1014 to perform baseline correction actions, such as described with reference to FIGS. 3a–3d. A window re-centering module 1016 performs actions to re-center chromatogram analysis windows, such as described with reference to FIGS. 4 and 5. A chromatogram reduction module 1018 performs actions to reduce chromatograms to comparable data sets, such as described with reference to FIGS. 6a and 6b. A chromatogram comparison module 1020 performs actions to compare chromatograms. A mapping and display module 1022 performs actions to map points on a cluster map. A bad data filter 1013 performs actions to identify potentially flawed chromatogram data. Each of these modules may access a memory device 1024 in chromatogram analysis module 1024. The chromatogram analysis module 1010 may communicate to a user station/display device 1026 to display data on a user interface 1028.

Some or all of the components in system 1002 of FIG. 10 or the process actions performed in the process of FIG. 2 may be implemented in hardware, in software, or as a combination of hardware and software. If implemented using hardware, any suitable hardware technology may be employed. For example, all or part of the chromatogram analysis module 1010 of FIG. 10 could be implemented using programmable logic devices such as a field programmable logic device ("FPGA"). If implemented using software, any suitable general purpose computer or dedicated programmable computing/processing device may be employed. The computer or computing device could comprise one or more processing units that perform specific operations executing one or more sequences of one or more instructions. The process performed by the invention may be implemented, transmitted, or stored as any "computer-usable medium," which as used herein, refers to any medium that provides information or is usable by a computer or processing/computing device. Such a medium may take many forms, including, but not limited to, non-volatile, volatile and transmission media. Non-volatile media includes media that can retain information in the absence of power. Volatile media includes media that can not retain information in the absence of power. Transmission media includes coaxial cables, copper wire and fiber optics, acoustic or light waves, and can also take the form of carrier waves; e.g., electromagnetic waves that can be modulated, as in frequency, amplitude or phase, to transmit information signals.

Therefore, described is a method and system for classification of chromatograms. An embodiment of the invention can be used for automated analysis of chromatographic traces with qualitative analysis, since data relating to peak shape is reduced and compared to data for other chromatograms. Since qualitative analysis is employed, the automated procedures can be employed for automated analysis of DHPLC chromatographic traces to detect sequence variations in DNA, which may cause changes in peak shapes rather than changes to direct quantitative measures. In the foregoing specification, the invention has been described with reference to specific embodiments thereof. It will, however, be evident that various modifications and changes may be made thereto without departing from the broader spirit and scope of the invention. For example, various combinations of process actions/steps have been described. However, additional or alternate process actions or combinations of process actions may also be employed in the invention within the spirit and scope of the invention. Thus, the specification and drawings are to be regarded in an illustrative rather than restrictive sense.

What is claimed is:

1. A computer implemented method for determining a similarity or dissimilarity between chromatogram data sets, comprising:
   a) receiving a chromatogram data;
   b) adjusting the chromatogram data in a region of interest by centering an analysis window around one or more trace features in the region of interest;
   c) reducing the chromatogram data to a data set, based at least on an average time for the chromatogram data in the region of interest by determining an integral of the chromatogram data and plotting against a time axis, determining a set of time points, and forming arrays of data set values based upon the set of time points and corresponding integral values for the set of time points;
   d) repeating the steps of (a) to (c) for at least one additional chromatogram data;
   e) choosing a reference data set from among the data sets obtained from the steps of (a) to (d); and
   f) comparing the reference data set to a remaining data set not chosen in step (e) to determine a similarity or dissimilarity between the reference data set and the remaining data set.

2. The method of claim 1, wherein the adjusting the chromatogram data comprises performing baseline correction.

3. The method of claim 1, further comprising:
   identifying the region of interest in the chromatogram data before adjusting the chromatogram data.

4. The method of claim 1, wherein the centering comprises:
   determining an average time for the region of interest; and
   centering the analysis window around the average time.

5. The method of claim 1, further comprising:
   establishing a threshold value for a peak characteristic selected from the group consisting of peak height, peak shape, peak position, peak slope, and peak size; and
   determining whether a value associated with the chromatogram data exceeds the threshold value, wherein the value exceeding the threshold value indicates the chromatogram data as bad data.

6. The method of claim 1, wherein the reducing comprises determining an array of data set values from the chromatogram data.

7. The method of claim 1, further comprising:
   mapping a result of the comparing.

8. The method of claim 7, wherein the mapping is performed to produce a two-dimensional cluster map.

9. The method of claim 1, wherein the comparing comprises determining a degree of similarity between the reference data set and the remaining data set.

10. The method of claim 1, wherein the comparing comprises determining a degree of dissimilarity between the reference data set and the remaining data set.

11. The method of claim 1, wherein the comparing comprises determining distance between vectors associated with the reference data set and the remaining data set.

12. The method of claim 1, wherein the chromatogram data relates to DNA analysis, and the reduced chromatogram data excludes a main DNA peak and encapsulates a possible sequence variation peak.

13. The method of claim 1, further comprising determining a presence of a sequence variation based on the comparing.

14. The method of claim 1, wherein the chromatogram data comprises DHPLC chromatogram data.

15. A system for comparing chromatograms, comprising:
   a data storage device to store chromatogram data;
   a communications interface adaptable to receive chromatogram data from the data storage device;
   a data adjustment module to adjust the chromatogram data;
   a reduction module to reduce the chromatogram data to a data set based at least on an average time for the chromatogram data in the region of interest by determining an integral of the chromatogram data and plotting against a time axis, determining a set of time points, and forming arrays of data set values based upon the set time points and corresponding integral values for the set of time points; and
   a comparison module to compare the reduced data set against other chromatogram data sets.

16. The system of claim 15, further comprising a data filter.

17. The system of claim 16, wherein the data filter performs filtering based upon criteria selected from the group consisting of peak height, peak area, peak shape, peak position, peek slope, and peak size.

18. The system of claim 15, wherein the data adjustment module performs baseline correction for the chromatogram data in a region of interest.

19. The system of claim 15, wherein the data adjustment module centers the analysis window around one or more trace features in a region of interest.

20. The system of claim 15, wherein the reduction module determines an array of data set values from the chromatogram data.

21. The system of claim 20, wherein the reduction module is configured to determine the array of data set values by:
selecting a set of time points in the first and second chromatogram data;
determining amplitude values corresponding to the set of time points; and
forming the arrays of data set values based upon the set of time points and their corresponding amplitude values.

22. The system of claim 15, wherein the reduction module determines an array of data set values by:
determining an integral of the chromatogram data and plotting against a time axis;
determining a set of time points;
forming the arrays of data set values based upon the set of time points and corresponding integral values for the set of time points.

23. The system of claim 15, wherein the data adjustment module, the reduction module, or the comparison module is implemented using one or more programmable logic devices.

24. The system of claim 15, further comprising a mapping module to map results from the comparison module.

25. The system of claim 24, further comprising a user interface to display results from the comparison module.

26. A computer usable medium having stored thereon a sequence of instructions which, when executed by a processor, causes the processor to execute a process for classifying chromatograms, said process comprising:
a) receiving a chromatogram data corresponding to a chromatogram;
b) adjusting the chromatogram data in a region of interest by centering an analysis window around one or more trace features in the region of interest;
c) reducing the chromatogram data to a data set, based at least on an average time for the chromatogram data the region of interest by determining an integral of the chromatogram data and plotting against a time axis, determining a set of time points, and forming arrays of data set values based upon the set of time points and corresponding integral values for the set of time points;
d) repeating the steps of (a) to (c) for at least one time;
e) choosing a reference data set from among the data set obtained from steps (a) to (d); and
f) comparing the reference data set to a remaining data set not chosen in step (e) to determine a similarity or dissimilarity between the reference data set and the remaining data set.

27. The method of claim 1, farther comprising determining the average time for chromatogram data in the region of interest.

28. The method of claim 27, wherein the determining the average time for chromatogram data in the region of interest is performed based on $$\bar{t} = \left(\sum_{i=0}^{i=n} y_i^2 * t_i\right) \bigg/ \sum_{i=0}^{i=n} y_i^2.$$

29. The medium of claim 26, wherein the adjusting comprises performing baseline correction.

30. The medium of claim 26, wherein the process further comprises:
identifying the region of interest in the chromatogram data before adjusting the chromatogram data.

31. The medium of claim 26, wherein the centering comprises:
determining an average time for the region of interest; and
centering the analysis window around the average time.

32. The medium of claim 26, wherein the process further comprises:
establishing a threshold value for a peak characteristic selected from the group consisting of peak height, peak shape, peak position, peak slope, and peak size; and
determining whether a value associated with the chromatogram data exceeds the threshold value, wherein the value exceeding the threshold value indicates the chromatogram data as bad data.

33. The medium of claim 26, wherein the reducing comprises determining an array of data set values from the chromatogram data.

34. The medium of claim 26, wherein the process further comprises:
mapping a result of the comparing.

35. The medium of claim 34, wherein the mapping is performed to produce a two-dimensional cluster map.

36. The medium of claim 26, wherein the comparing comprises determining a degree of similarity between the reference data set and the remaining data set.

37. The medium of claim 26, wherein the comparing comprises determining a degree of dissimilarity between the reference data set and the remaining data set.

38. The medium of claim 26, wherein comparing comprises determining distance between vectors associated with the reference data set and the remaining data set.

39. The medium of claim 26, wherein the chromatogram data relates to DNA analysis, and the reduced chromatogram data excludes a main DNA peak and encapsulates a possible sequence variation peak.

* * * * *